(12) United States Patent
Trofast et al.

(10) Patent No.: US 7,354,913 B2
(45) Date of Patent: *Apr. 8, 2008

(54) HIGH STORAGE STABILITY INHALABLE COMPOSITIONS

(75) Inventors: Eva Trofast, Lund (SE); Karin Malmqvist-Granlund, Lund (SE); Per-Gunnar Nilsson, Lund (SE); Kyrre Thalberg, Lund (SE)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/054,707

(22) Filed: Feb. 8, 2005

(65) Prior Publication Data

US 2005/0207989 A1    Sep. 22, 2005

Related U.S. Application Data

(63) Continuation of application No. 10/276,497, filed as application No. PCT/SE01/01118 on May 17, 2001, now Pat. No. 6,869,942.

(30) Foreign Application Priority Data

May 19, 2000 (GB) .................................. 0012260.6

(51) Int. Cl.
*A61K 31/135* (2006.01)
*A61K 31/56* (2006.01)

(52) U.S. Cl. ........................ 514/171; 514/653; 514/826

(58) Field of Classification Search ...................... None
See application file for complete search history.

(56) References Cited

U.S. PATENT DOCUMENTS

| | | | |
|---|---|---|---|
| 5,637,620 A * | 6/1997 | Trofast et al. .............. | 514/630 |
| 5,795,564 A | 8/1998 | Aberg et al. | |
| 5,874,063 A * | 2/1999 | Briggner et al. .............. | 424/45 |
| 6,030,604 A | 2/2000 | Trofast | |
| 6,869,942 B2 * | 3/2005 | Trofast et al. .............. | 514/171 |

FOREIGN PATENT DOCUMENTS

| | | |
|---|---|---|
| EP | 1 014 993 | 8/2002 |
| EP | 1 156 790 B1 | 6/2003 |
| EP | 1 152 753 B1 | 5/2004 |
| WO | WO 98/15280 | 4/1998 |
| WO | WO 9831351 A1 | 7/1998 |
| WO | WO 99/15182 | 4/1999 |
| WO | WO 99/64014 | 12/1999 |
| WO | WO 00/28979 | 5/2000 |
| WO | WO 01/78693 A2 | 10/2001 |
| WO | WO 01/78745 A1 | 10/2001 |

OTHER PUBLICATIONS

Remington's Pharmaceutical Sciences, published 1980 by Mack Publishing Company, 16th edition, pp. 431-435.*
Comparative Data provided by Chiesi Farmaceutica S.p.A. during European Opposition proceedings (document D6 from opposition), 2 pages.
Zeng et al., "Effects of particle size and adding sequence of fine lactose on the deposition of salbutamol sulphate from a dry powder formulation," International Journal of Pharmaceutics, 182 (1999), pp. 133-144.
Zeng et al., "Particulate Interactions in Dry Powder Formulations for Inhalation," Taylor & Francis (2001), pp. 30, 31 and 159-161.

* cited by examiner

*Primary Examiner*—Raymond J. Henley, III
(74) *Attorney, Agent, or Firm*—Fish & Richardson, P.C.

(57) ABSTRACT

Inhalable pharmaceutical compositions are provided, for use in the treatment of respiratory disorders such as asthma, rhinitis and chronic obstructive pulmonary disease (COPD). These compositions have high storage stability, and include formoterol and a corticosteroid.

7 Claims, 3 Drawing Sheets

HIGH STORAGE STABILITY INHALABLE COMPOSITIONS

CROSS REFERENCE TO RELATED APPLICATION

The present application is a continuation of application Ser. No. 10/276,497, filed Nov. 15, 2002, now U.S. Pat. No. 6,869,942, which is a national phase application under 35 U.S.C. Section 371 filed from International Patent Application PCT/SE01/01118, filed 17 May 2001, which claims priority to United Kingdom patent application Serial No. 0012260.6, filed 19 May 2000. The contents of these applications are incorporated herein by reference in their entirety.

FIELD OF THE INVENTION

The present invention relates to a stable powder formulation comprising formoterol or enantiomers of formoterol, a glucocorticosteroid and a carrier or diluent for use in the treatment of inflammatory conditions/disorders, especially respiratory diseases such as asthma, COPD and rhinitis.

BACKGROUND OF THE INVENTION

Stability is one of the most important factors which determines whether a compound or a mixture of compounds can be developed into a therapeutically useful pharmaceutical product. When mixing different ingredients in a pharmaceutical formulation there exists the possibility of interactions taking place between the components. In addition, each component may have different degradation characteristics.

Formoterol is a highly potent and selective β2-agonist with a long duration of action when inhaled. Compared to other β-adrenergic compounds it has a unique chemical structure with a formamido group substituted on the benzene ring. It has two asymmetric carbon atoms in the molecule making four stereoisomers possible. Most studies, clinical and preclinical, appear to have been performed with the fumarate (as dihydrate) of the enantiomeric mixture designed R;R+S;S. The R;R enantiomer is the most potent of the four enantiomers.

The stability profile of the drug formoterol (mainly as fumarate dihydrate) has been evaluated by investigating the influence of variables such as storage time, temperature, relative humidity, light and pH on the content of formoterol and determining the amount of chromatographic impurities. Formoterol (as fumarate dihydrate) has been demonstrated to be stable under long-term storage even at high temperatures and high relative humidities.

However, the chemical structure of formoterol makes the molecule prone to chemical degradation when in contact with e.g. a reactive species like an aldehyde or under stress conditions e.g. a milling process.

Potent drugs for administration by inhalation are generally formulated in association with carriers/diluents such as lactose to facilitate accurate dosing from an inhaler. These formulations have generally consisted of coarse particles of a carrier together with fine particles of the drug(s), optionally together with small particles of carrier/diluent, which combination is generally known as an ordered mixture. An alternative to such a formulation is to agglomerate the small particles of the drug(s) and the carrier/diluent to agglomerates.

Formoterol (as fumarate dihydrate) as well as a carbohydrate such as lactose (preferably as the monohydrate) are very stable compounds individually, but degradation products are formed when the two compounds are mixed. A mixture of formoterol fumarate dihydrate and lactose monohydrate can be regarded as a three component system composed of formoterol fumarate, lactose and water. By sorption of water a saturated aqueous lactose solution is formed at the surface of the powder mixture. A certain amount of formoterol fumarate dissolves in this aqueous solution and is thereby susceptible to degradation. Therefore, the relative humidity, as well as the storage temperature, will influence the stability of the powder mixture.

When adding a third ingredient in the mixture the formation of degradation products would be expected to be higher due to the complexity and the possibility for many degradation processes. It would therefore be desirable to develop a formulation with good stability in spite of the complex mixture of compounds having reactive chemical functions such as an amine (formoterol), formamide (formoterol), carbohydrate (e.g. lactose) and a keto function (glucocorticosteroid). The presence of hydrates (formoterol fumarate dihydrate, lactose monohydrate) will make it even more complex.

DESCRIPTION OF THE INVENTION

Figure 1:
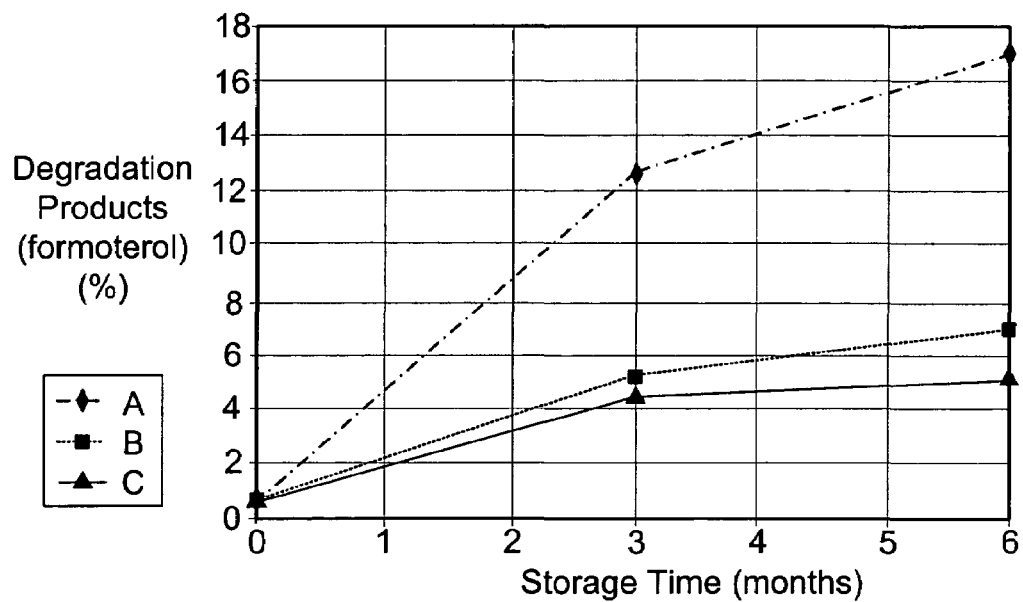
FIG. 1 is a graph depicting stability data for various inhalable compositions stored in open dishes.

In accordance with the present invention, there is provided a pharmaceutical composition in the solid state comprising, in admixture, a first active ingredient which is micronised formoterol or an enantiomer thereof, a second active ingredient which is a micronised glucocorticosteroid and a carrier or diluent, the composition having a high storage stability.

By the term "high storage stability" is meant that the decomposition of formoterol in the formulation will be less than 10% when stored in open dishes at 40° C. and 75% relative humidity for 6 months when the content of formoterol is less than about 1.0% (w/w), preferably less than 0.8% (w/w) and most preferably less than about 0.6% (w/w) in the formulation or, when stored in a dry powder device, a decomposition of less than about 2.5% under the same conditions.

The formulations having the desired stability are prepared using a novel process which involves:
1. preparing a mixture of micronised first active ingredient and micronised carrier/diluent
2. optionally adding further micronised carrier/diluent to the mixture
3. addition and mixing of pre-micronised hydrophobic second active ingredient, the second active ingredient being optionally pre-mixed with micronised carrier/diluent, and
4. either subjecting the mixture to agglomeration and spheronisation, or adding coarse carrier/diluent.

The first active ingredient and carrier/diluent can be prepared according to step 1 by micronising the two components together or each can be micronised individually and then combined to give a micronised mixture. Preferably the two components are mixed together and then micronised.

Preferably at step 3 the pre-micronised hydrophobic second active ingredient is added alone, ie in the absence of further micronised carrier/diluent.

Preferably step 4 involves subjecting the mixture to agglomeration and spheronisation.

By "micronised" is meant milling to give the a desired particle size or obtaining a desired particle size by any other means for producing small particles such as direct precipitation.

Optionally the mixture/ingredients can be conditioned at any suitable stage of the process, such as between steps 1 and 2, and/or the further pre-micronised carrier/diluent can be conditioned prior to addition at step 2, and/or the further pre-micronised carrier/diluent can be conditioned prior to addition at step 3, and/or the mixture can be conditioned between the agglomeration and spheronisation in step 4.

Conditioning can be carried out according to the procedures described in WO 95/05805 or by selecting the process parameters such as relative humidity in such a way that the final product when submitted to water vapour gives off heat of less than 1.2 joules per gram for the particles having a mean particle size of less than 10 μm as described and measured in U.S. Pat. No. 5,874,063.

The invention therefore provides a pharmaceutical formulation in the solid state comprising, in admixture, a first active ingredient which is micronised formoterol or an enantiomer thereof, a second active ingredient which is a micronised glucocorticosteroid and a carrier/diluent and having a high storage stability characterised in that the formulation is prepared by micronisation of the first active ingredient and carrier/diluent, optionally followed by mixing pre-micronised coarser carrier/diluent, mixing with micronised hydrophobic second active ingredient, and finally either subjecting the mixture to agglomeration and spheronisation or adding coarse carrier/diluent.

The formoterol can be in the form of a mixture of enantiomers. Preferably the formoterol is in the form of a single enantiomer, preferably the R;R enantiomer. The formoterol can be in the form of the free base, salt or solvate, or a solvate of a salt, preferably the formoterol is in the form of its fumarate dihydrate salt. Other suitable physiologically salts include chloride, bromide, sulphate, phosphate, maleate, tartrate, citrate, benzoate, 4-methoxybenzoate, 2- or 4-hydroxybenzoate, 4-chlorobenzoate, p-toluenesulphonate, benzenesulphonate, ascorbate, acetate, succinate, lactate, glutarate, gluconate, tricaballate, hydroxynapaphthalenecarboxylate or oleate.

Preferably the second active ingredient is a micronised glucocorticosteroid such as budesonide, fluticasone propionate, mometasone furoate, ciclesonide and epimers, esters, salts and solvates of these compounds. More preferably the second active ingredient is budesonide or an epimer thereof, most preferably the 22R-epimer of budesonide.

Preferably the carrier is a carbohydrate having a high storage stability, preferably a reducing carbohydrate such as lactose, glucose, galactose, mannose, xylose, maltose, cellobiose, mellibiose, maltotriose (e.g. as monohydrate). More preferably the carrier is lactose.

As used herein the term micronised carrier/diluent refers to carrier/diluent having a mean particle size of less than about 25 μm, preferably less than about 10 μm, more preferable less than about 5 μm. The micronised carrier can be produced using processes known in the art such as micronisation or direct precipitation. The term coarse carrier/diluent refers to carrier/diluent having a mean particle size of greater than about 25 μm.

As used herein the term micronised first active ingredient or micronised second active ingredient means active ingredient having a mean particle size of less than about 10 μm, preferably less than about 5 μm.

The pharmaceutical compositions according to the invention can be used for the treatment or prophylaxis of a respiratory disorder, in particular the treatment or prophylaxis of asthma, rhinitis or COPD.

In a further aspect the invention provides a method of treating a respiratory disorder, in particular asthma, rhinitis or COPD, in a mammal which comprises administering to a patient a pharmaceutical composition as herein defined.

The compositions of the invention can be inhaled from a nebulizer, from a pressurized metered dose inhaler or as a dry powder from a dry powder inhaler e.g. multidose reservoir systems from AstraZeneca (Turbuhaler®) or Schering-Plough or from a dry powder inhaler utilizing gelatine, plastic or other capsules, cartridges or blister packs. Doses will be dependent on the severity of the disease and the type of patient.

Figure 3:
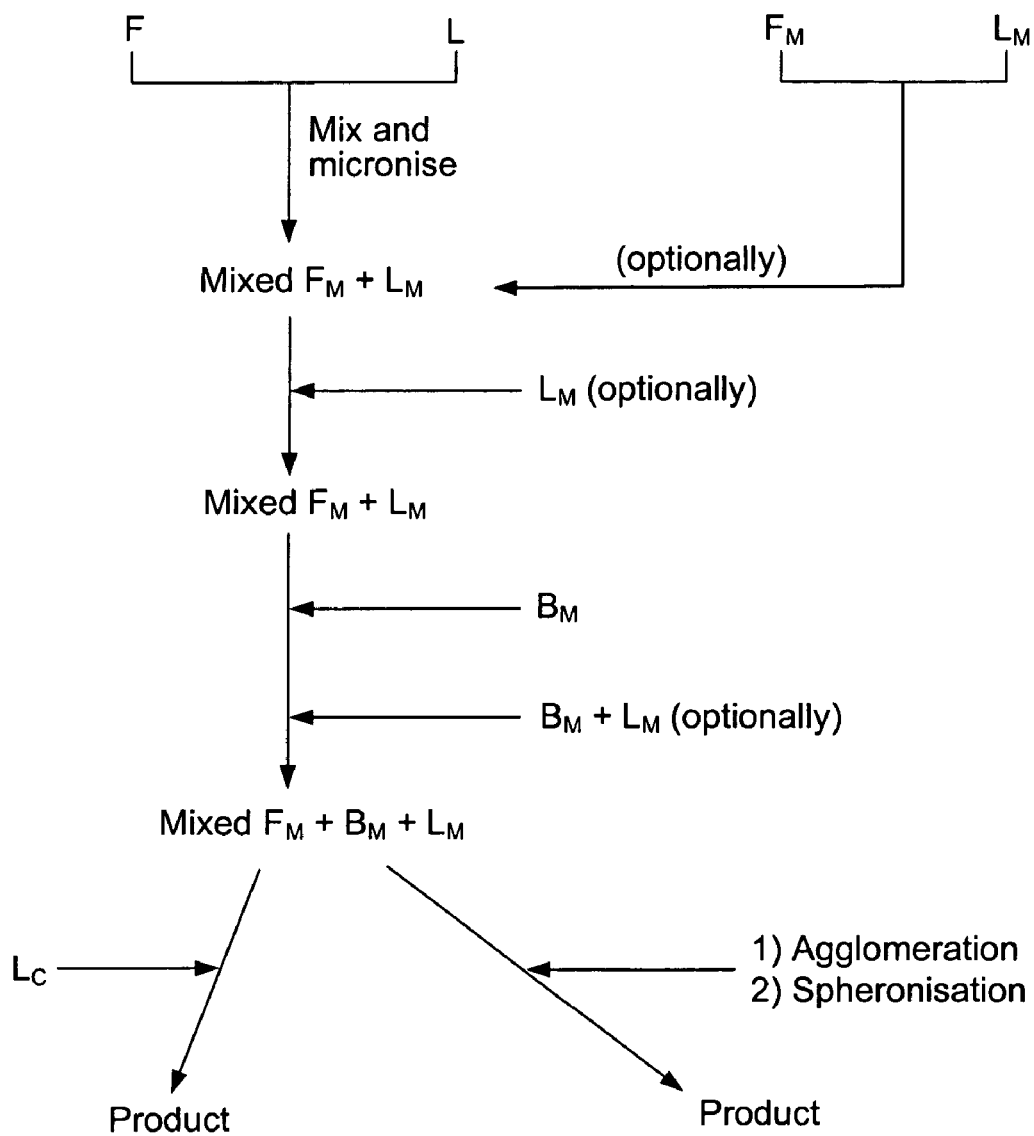
FIG. 3 is flow chart illustrating processes for forming a pharmaceutical composition as disclosed herein.

The process of the invention is shown schematically in FIG. 3.

The reference letters in FIG. 3 have the following significance:

L=carrier/diluent
F=formoterol
$L_C$=coarse particles of carrier/diluent
$L_M$=small particles of carrier/diluent produced by methods like micronisation, direct precipitation etc.
$F_M$=small particles of formoterol produced by methods like micronisation, direct precipitation etc.
$B_M$=small particles of glucocorticosteroid produced by methods like micronisation, direct precipitation etc.

Experimental Section

The invention is illustrated by the following examples which are not intended to limit the scope of the application. In the examples micronisation is carried out such that the particle size range for each of the active components is suitable for administration by inhalation. The determination of the formoterol degradation products was performed by reversed phase liquid chromatography, on a two column system using LiChrospher 60 RP-select B. 5 μm particles with octylsilane as stationary phase. UV-detector at 214 nm. Evaluation was done as area-% since the degradation products were not fully known.

EXAMPLE 1

The following example is a reference example in which the formulation is prepared in a conventional manner.

Formoterol fumarate dihydrate (26 g) and lactose monohydrate (4.974 kg) are mixed for one or two hours in a tumbling mixer. This mixture was micronised in a spiral jet mill in order to attain a particle size suitable for inhalation. Micronisation of substances into the low micron range (1-5 μm) may induce disturbances in the crystallinity of the substance. Amorphous areas are introduced, especially at the surfaces of the micronised substance. This morphological change of the substances will increase the sensitivity to humidity and thereby being an potential implement to stability problems. The crystal structure of the substance mixture was restored in a controlled way according to U.S. Pat. No. 5,874,063 or U.S. Pat. No. 5,709,884.

To improve the flowability of the cohesive powder it was spheronised to agglomerates at room temperature at a controlled relative humidity of less than 50%.

Stability data of a formoterol fumarate dihydrate (5 mg/g)/lactose monohydrate (995 mg/g) micronised mixture and stored in open dishes at 40° C. and 75% relative humidity for 6 months. Results see FIG. 1(A).

In FIG. 1, A represents formoterol fumarate dihydrate (0.5%)/lactose monohydrate (99.5%) according to example 1, B represents formoterol fumarate dihydrate (0.5%)/budesonide (9%)/lactose monohydrate (90.5%), and C represents formoterol fumarate dihydrate (0.5%)/budesonide (18%)/lactose monohydrate (81.5%).

EXAMPLE 2

The following example is a reference example in which the formulation is prepared in a conventional manner.

The micronised and spheronised formoterol fumarate dihydrate/lactose monohydrate formulation according to example 1 was filled in the powder device Turbuhaler® (AstraZeneca) and stored for 6 months at 40° C. and 75% relative humidity. Results see FIG. 2(A).

Figure 2:
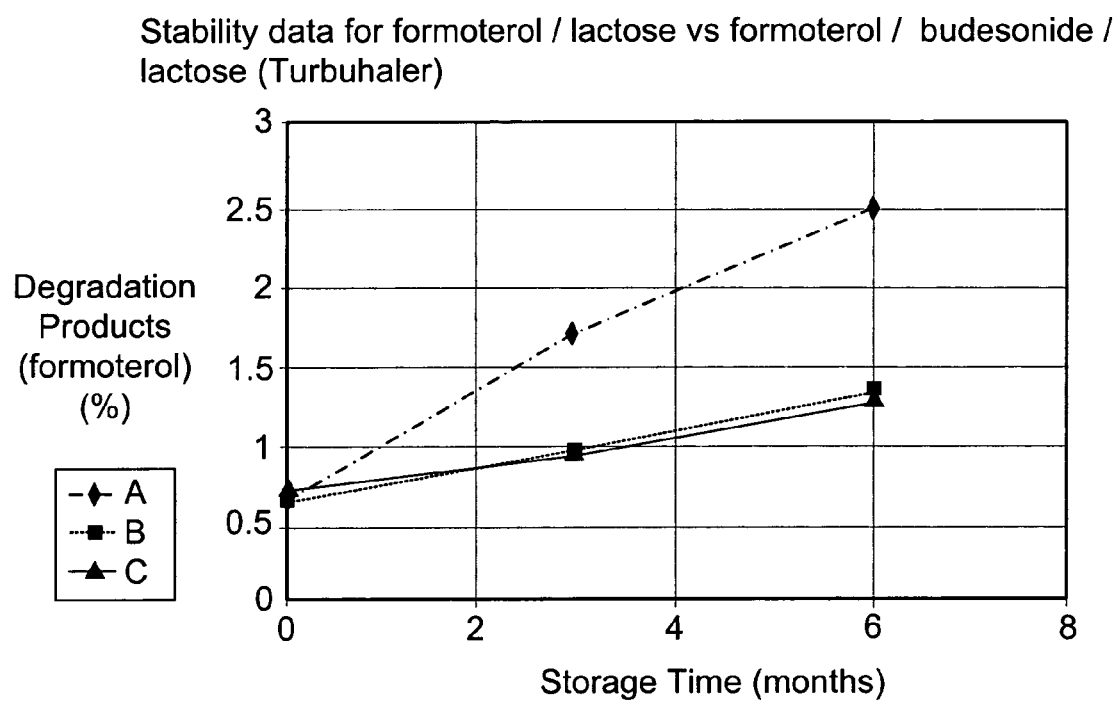
FIG. 2 is a graph depicting stability date for various inhalable composition stored in dry powder inhalers.

In FIG. 2, A represents formoterol fumarate dihydrate (0.5%)/lactose monohydrate (99.5%); 4.5 µg formoterol fumarate dihydrate/dose according to example 2; B represents formoterol fumarate dihydrate (0.5%)/budesonide (9%)/lactose monohydrate (90.5%); 4.5 µg formoterol fumarate dihydrate/80 µg budesonide/dose; and C represents formoterol fumarate dihydrate (0.5%)/budesonide (18%)/lactose monohydrate (81.5%); 4.5 µg formoterol fumarate dihydrate/160 µg budesonide/dose.

EXAMPLE 3

Formoterol fumarate dihydrate (0.2 kg) and lactose monohydrate (34 kg) are mixed for one or two hours in a tumbling mixer. This mixture was micronised in a spiral jet mill in order to attain a particle size suitable for inhalation. The crystal structure was restored in a controlled way according to U.S. Pat. No. 5,874,063 or U.S. Pat. No. 5,709,884. This conditioned product is mixed with micronised budesonide (3 kg) for thirty to sixty minutes in a tumbling mixer. As a second mixing step the powder was fed to a modified spiral jet mill, operating at a very low milling pressure and a high flow of nitrogen. This will break up agglomerates without causing a further size reduction of the particles (and thereby creating amorphous areas and as a consequence loss of stability) while improving the homogeneous distribution of budesonide in the powder.

To improve the flowability of the cohesive powder it was spheronised to agglomerates at room temperature at a controlled relative humidity of less than 50%.

Stability data of a formoterol fumarate dihydrate (5 mg/g)/budesonide (90 mg/g)/lactose monohydrate (905 mg/g) micronised mixture and stored in open dishes at 40° C. and 75% relative humidity for 6 months. Results see FIG. 1(B).

EXAMPLE 4

The micronised and spheronised formoterol fumarate dihydrate (5 mg/g)/budesonide (90 mg/g)/lactose monohydrate (905 mg/g) according to example 3 was filled in the dry powder device Turbuhaler® (AstraZeneca) and stored for 6 months at 40° C. and 75% relative humidity. Results see FIG. 2(B).

The invention claimed is:

1. A pharmaceutical composition comprising, in admixture, a first active ingredient which is micronised formoterol optionally in the form of a salt or solvate of a salt, a second active ingredient which is a micronised glucocorticosteroid, and a pharmaceutically acceptable carrier/diluent, wherein the composition is obtained by a process comprising:
   (a) preparing a mixture of the first active ingredient and a first portion of the carrier/diluent, both being in micronized form, and having a mean particle size of less than 10 µm;
   (b) adding the second active ingredient in pre-micronized form and having a mean particle size of less than 10 µm, to the mixture of a step (a) and mixing;
   (c) subsequent to step (b), adding a second portion of the carrier/diluent, in coarse form, having a mean particle size of greater than 25 µm, to form a composition;
   wherein no micronization step is performed subsequent to step (c), and wherein the composition is in the form of an ordered mixture in which each of the active ingredients has a particle size less than 10 µm, the first portion of the carrier/diluent has a mean particle size of less than 10 µm, and the second portion of the carrier/diluent has a mean particle size of greater than 25 µm, and the composition has a high storage stability such that the decomposition of formoterol in the composition will be less than 10% when (i) the composition is stored in open dishes at 40° C. and 75% relative humidity for 6 months and (ii) the content of formoterol in the composition is less than 1.0% (w/w).

2. A pharmaceutical composition according to claim 1 in which the formoterol is in the form of its fumarate dihydrate salt.

3. A pharmaceutical composition according to claim 1 in which the formoterol is in the form of its single R,R-enantiomer.

4. A pharmaceutical composition according to claim 1 in which the second active ingredient is budesonide.

5. A pharmaceutical composition according to claim 1 in which the second active ingredient is the 22R-epimer of budesonide.

6. A pharmaceutical composition according to claim 1 in which the carrier/diluent is lactose.

7. A pharmaceutical composition comprising, in admixture, a first active ingredient which is micronised formoterol optionally in the form of a salt or solvate of a salt, a second active ingredient which is a micronised glucocorticosteroid, and a first and second portion of a pharmaceutically acceptable carrier/diluent, wherein at least a portion of the carrier/diluent is in coarse form, the composition is in the form of an ordered mixture in which each of the active ingredients has a particle size less than 10 µm, the first portion of the carrier/diluent has a mean particle size of less than 10 µm, and the second portion of the carrier/diluent has a mean particle size of greater than 25 µm, and the composition has a high storage stability such that the decomposition of formoterol in the composition will be less than 10% when (i) the composition is stored in open dishes at 40° C. and 75% relative humidity for 6 months and (ii) the content of formoterol in the composition is less than 1.0% (w/w).

* * * * *

UNITED STATES PATENT AND TRADEMARK OFFICE
CERTIFICATE OF CORRECTION

PATENT NO. : 7,354,913 B2
APPLICATION NO. : 11/054707
DATED : April 8, 2008
INVENTOR(S) : Eva Trofast et al.

It is certified that error appears in the above-identified patent and that said Letters Patent is hereby corrected as shown below:

On the Title Page, Column 2, Section (74), after "Richardson," delete ",".

In Claim 1, Column 6, Line 10, after "form" delete ",".

In Claim 1, Column 6, Line 12, after "ingredient" insert --,--.

In Claim 1, Column 6, Line 14, after "mixture of" delete "a".

In Claim 1, Column 6, Line 23, after "10 μm" delete ",".

In Claim 7, Column 6, Line 54, after "10 μm" delete ",".

Signed and Sealed this

Twenty-second Day of July, 2008

JON W. DUDAS
*Director of the United States Patent and Trademark Office*